US011109870B2

(12) United States Patent
Kipshidze et al.

(10) Patent No.: US 11,109,870 B2
(45) Date of Patent: Sep. 7, 2021

(54) CONTROLLING THE DELIVERY OF EMBOLIC BEADS INTO AN ARTERY

(71) Applicant: Endobar Solutions LLC, Orangeburg, NY (US)

(72) Inventors: Nickolas Kipshidze, New York, NY (US); Eran Levit, Amherst, NH (US)

(73) Assignee: Endobar Solutions LLC, Orangeburg, NY (US)

( * ) Notice: Subject to any disclaimer, the term of this patent is extended or adjusted under 35 U.S.C. 154(b) by 271 days.

(21) Appl. No.: 15/843,288

(22) Filed: Dec. 15, 2017

(65) Prior Publication Data

US 2018/0168661 A1 Jun. 21, 2018

Related U.S. Application Data

(60) Provisional application No. 62/435,217, filed on Dec. 16, 2016.

(51) Int. Cl.
*A61B 17/12* (2006.01)
*A61M 39/22* (2006.01)
(Continued)

(52) U.S. Cl.
CPC .. *A61B 17/12186* (2013.01); *A61B 17/12109* (2013.01); *A61M 5/16827* (2013.01);
(Continued)

(58) Field of Classification Search
CPC ........ A61M 5/1408; A61M 2005/1402; A61M 5/16827; A61M 5/007; A61M 31/005;
A61M 39/223; A61M 2039/224; A61M 2039/229; A61M 39/225; A61M 5/3146; A61M 2205/3337; A61M 2205/3344;
(Continued)

(56) References Cited

U.S. PATENT DOCUMENTS 4,604,093 A * 8/1986 Brown .............. A61M 5/16827
137/625.11
9,572,700 B1 2/2017 Kipshidze et al.
(Continued)

FOREIGN PATENT DOCUMENTS

WO 2005110007 A2 11/2005
WO 2007002154 A2 1/2007
(Continued)

OTHER PUBLICATIONS

International Search Report and Written Opinion for application PCT/US2017/066588 dated Mar. 29, 2018.

*Primary Examiner* — Lauren P Farrar
(74) *Attorney, Agent, or Firm* — Potomac Law Group, PLLC

(57) ABSTRACT

Controlled delivery of embolic beads into a subject's artery is achieved using a pump configured to draw fluid into a chamber and eject fluid from the chamber, one or more valves that control fluid-flow paths between three ports and the chamber of the pump, a valve actuator that places the one or more valves into various operating states, and a controller that controls the operation of the pump and the one or more valves in a controlled sequence. The various operating states interconnect one of the ports with a common port in fluid communication with the pump to achieve the controlled delivery of embolic beads.

10 Claims, 8 Drawing Sheets

(51) Int. Cl.
*A61M 5/168* (2006.01)
*A61B 17/00* (2006.01)
*A61M 5/31* (2006.01)

(52) U.S. Cl.
CPC ........ *A61M 39/223* (2013.01); *A61M 39/225* (2013.01); *A61B 2017/00398* (2013.01); *A61B 2017/00734* (2013.01); *A61B 2017/1205* (2013.01); *A61M 5/3146* (2013.01); *A61M 2205/3337* (2013.01); *A61M 2205/3344* (2013.01)

(58) Field of Classification Search
CPC ........ A61B 17/12186; A61B 17/12109; A61B 2017/00398; A61B 2017/00734; A61B 2017/1205
See application file for complete search history.

(56) References Cited

U.S. PATENT DOCUMENTS

| | | | | |
|---|---|---|---|---|
| 2007/0197963 | A1* | 8/2007 | Griffiths | A61M 5/007 604/97.01 |
| 2014/0224829 | A1* | 8/2014 | Capone | F04B 49/06 222/23 |
| 2015/0133780 | A1 | 5/2015 | Kipshidze et al. | |
| 2015/0335453 | A1 | 11/2015 | Kipshidze et al. | |
| 2015/0359540 | A1* | 12/2015 | Kipshidze | A61B 17/12031 604/510 |

FOREIGN PATENT DOCUMENTS

| | | |
|---|---|---|
| WO | 2009058124 A1 | 5/2009 |
| WO | 2015036626 A1 | 3/2015 |

\* cited by examiner

CONTROLLING THE DELIVERY OF EMBOLIC BEADS INTO AN ARTERY

CROSS REFERENCE TO RELATED APPLICATIONS

This Application claims the benefit of U.S. Provisional Application 62/435,217 filed Dec. 16, 2016, which is incorporated herein by reference in its entirety.

BACKGROUND

U.S. Pat. No. 9,572,700, which is incorporated herein by reference in its entirety, describes a treatment for obesity by selectively delivering embolic particles into the distal portion of the left gastric artery via a catheter.

When delivering embolic particles into an artery, care must be taken to ensure that the embolic particles do not back up in a proximal direction to prevent embolic particles from lodging in non-target arteries. One way to prevent embolic particles from backing up is to seal the space between the outer wall of the catheter and the inner wall of the artery with an inflated balloon. But even when this approach is used, conventional approaches to delivering embolic particles via a catheter can be problematic.

SUMMARY OF THE INVENTION

One aspect of the invention is directed to a first apparatus for controlling the delivery of embolic beads into a subject's artery via a lumen of a catheter. The first apparatus comprises an internal syringe, a linear actuator, a valve, a valve actuator, first and second inlet ports, a first outlet port, a first fluid flow path and a controller. The internal syringe includes a chamber configured to hold fluid, the chamber having an orifice, and the internal syringe has a plunger configured to draw fluid into the chamber via the orifice when the plunger is withdrawn and eject fluid out of the chamber via the orifice when the plunger is advanced. The linear actuator is operatively connected to the plunger such that the linear actuator (i) withdraws the plunger in response to a draw control signal and (ii) advances the plunger in response to an eject control signal. The valve has a common port arranged in fluid communication with the orifice, a first port, a second port, and a third port, and the valve has a first operating state in which a fluid-flow path is provided between the first port and the common port, a second operating state in which a fluid-flow path is provided between the second port and the common port, and a third operating state in which a fluid-flow path is provided between the third port and the common port. The valve actuator is operatively connected to the valve such that the valve actuator (a) places the valve in the first operating state in response to a first valve control signal, (b) places the valve in the second operating state in response to a second valve control signal, and (c) places the valve in the third operating state in response to a third valve control signal. The first inlet port is arranged in fluid communication with the first port of the valve, and the first inlet port is configured to provide a fluid-tight coupling with an orifice of an external syringe when the external syringe is connected to the first inlet port. The first outlet port is arranged in fluid communication with the second port of the valve, and the first outlet port is configured to provide a fluid-tight connection with the lumen of the catheter when the catheter is connected to the first outlet port. The second inlet port is arranged to provide a fluid-tight coupling with a source of saline solution. The first fluid flow path is arranged to route saline solution arriving via the second inlet port into the third port of the valve. And the controller is configured to generate the draw control signal, the eject control signal, the first valve control signal, the second valve control signal, and the third valve control signal in a controlled sequence.

In some embodiments of the first apparatus, the generation of the draw control signal, the eject control signal, the first valve control signal, the second valve control signal, and the third valve control signal in the controlled sequence causes the linear actuator and the valve actuator to control the internal syringe and the valve, respectively, to implement the steps of: (a) drawing a first volume of saline into the chamber via the second inlet port and via the third port of the valve; (b) subsequent to step (a), ejecting at least a portion of the first volume of saline out of the chamber to de-air the internal syringe; (c) subsequent to step (b), drawing a second volume of saline into the chamber via the second inlet port and via the third port of the valve; (d) subsequent to step (c), ejecting a first portion of the second volume of saline out of the chamber and out of the first inlet port via the first port of the valve to de-air the first inlet port; (e) subsequent to step (c), ejecting a second portion of the second volume of saline out of the chamber and out of the first outlet port via the second port of the valve to de-air the first outlet port; (f) subsequent to steps (d) and (e), and subsequent to a connection of an external syringe filled with a fluid containing embolic beads to the first inlet port, drawing a fluid containing embolic beads into the chamber via the first inlet port and the first port of the valve; and (g) subsequent to step (f), ejecting the fluid containing the embolic beads out of the chamber and out of the first outlet port via the second port of the valve. In some of these embodiments, the generation of the draw control signal, the eject control signal, the first valve control signal, the second valve control signal, and the third valve control signal in the controlled sequence also causes the linear actuator and the valve actuator to control the internal syringe and the valve, respectively, to implement the steps of: (h) subsequent to step (g), drawing a third volume of saline into the chamber via the second inlet port and via the third port of the valve; and (i) subsequent to step (h), ejecting at least a portion of the third volume of saline out of the chamber and out of the first outlet port via the second port of the valve.

Some embodiments of the first apparatus further comprise a sensor arranged to detect when the external syringe is connected to the first inlet port and report a connection status of the external syringe to the controller.

Some embodiments of the first apparatus further comprise a pressure gauge arranged to measure a fluid pressure of fluid exiting the first outlet port and report a fluid pressure measurement to the controller.

Some embodiments of the first apparatus further comprise a drain port and a second fluid flow path arranged to route fluid from the third port of the valve to the drain port, wherein the first fluid flow path includes a first check valve, and the second fluid flow path includes a second check valve.

In some embodiments of the first apparatus, the valve comprises a rotary valve having at least three positions, and the valve actuator comprises a motor configured to move the rotary valve between the at least three positions.

Some embodiments of the first apparatus further comprise a sensor arranged to detect when the external syringe is connected to the first inlet port and report a connection status of the external syringe to the controller, a pressure gauge arranged to measure a fluid pressure of fluid exiting the first outlet port and report a fluid pressure measurement to the controller, a drain port, and a second fluid flow path arranged to route fluid from the third port of the valve to the drain port. In these embodiments, the first fluid flow path includes a first check valve, and the second fluid flow path includes a second check valve. In some of these embodiments, the generation of the draw control signal, the eject control signal, the first valve control signal, the second valve control signal, and the third valve control signal in the controlled sequence causes the linear actuator and the valve actuator to control the internal syringe and the valve, respectively, to implement the steps of: (a) drawing a first volume of saline into the chamber via the second inlet port and via the third port of the valve; (b) subsequent to step (a), ejecting at least a portion of the first volume of saline out of the chamber via the drain port to de-air the internal syringe; (c) subsequent to step (b), drawing a second volume of saline into the chamber via the second inlet port and via the third port of the valve; (d) subsequent to step (c), ejecting a first portion of the second volume of saline out of the chamber and out of the first inlet port via the first port of the valve to de-air the first inlet port; (e) subsequent to step (c), ejecting a second portion of the second volume of saline out of the chamber and out of the first outlet port via the second port of the valve to de-air the first outlet port; (f) subsequent to steps (d) and (e), and subsequent to a connection of an external syringe filled with a fluid containing embolic beads to the first inlet port, drawing a fluid containing embolic beads into the chamber via the first inlet port and the first port of the valve; and (g) subsequent to step (f), ejecting the fluid containing the embolic beads out of the chamber and out of the first outlet port via the second port of the valve, wherein the controller is configured to abort step (g) if the fluid pressure measurement reported to the controller exceeds a threshold.

In some of these embodiments, the generation of the draw control signal, the eject control signal, the first valve control signal, the second valve control signal, and the third valve control signal in the controlled sequence also causes the linear actuator and the valve actuator to control the internal syringe and the valve, respectively, to implement the steps of: (h) subsequent to step (g), drawing a third volume of saline into the chamber via the second inlet port and via the third port of the valve; and (i) subsequent to step (h), ejecting at least a portion of the third volume of saline out of the chamber and out of the first outlet port via the second port of the valve.

Another aspect of the invention is directed to a second apparatus for controlling the delivery of embolic beads into a subject's artery via a lumen of a catheter. The second apparatus comprises a pump, at least one valve, a valve actuator, a first inlet port, a first outlet port, a second inlet port, a first fluid flow path, and a controller. The pump is configured to draw fluid into a chamber in response to a draw control signal and eject fluid from the chamber in response to an eject control signal. The at least one valve has a common port arranged in fluid communication with the pump, a first port, a second port, and a third port, and the at least one valve has a first operating state in which a fluid-flow path is provided between the first port and the common port, a second operating state in which a fluid-flow path is provided between the second port and the common port, and a third operating state in which a fluid-flow path is provided between the third port and the common port. The valve actuator is operatively connected to the at least one valve such that the valve actuator (a) places the at least one valve in the first operating state in response to a first valve control signal, (b) places the at least one valve in the second operating state in response to a second valve control signal, and (c) places the at least one valve in the third operating state in response to a third valve control signal. The first inlet port is arranged in fluid communication with the first port of the at least one valve, and the first inlet port is configured to provide a fluid-tight coupling with an orifice of an external syringe when the external syringe is connected to the first inlet port. The first outlet port is arranged in fluid communication with the second port of the at least one valve, and the first outlet port is configured to provide a fluid-tight connection with the lumen of the catheter when the catheter is connected to the first outlet port. The second inlet port is arranged to provide a fluid-tight coupling with a source of saline solution. The first fluid flow path is arranged to route saline solution arriving via the second inlet port into the third port of the at least one valve. And the controller is configured to generate the draw control signal, the eject control signal, the first valve control signal, the second valve control signal, and the third valve control signal in a controlled sequence.

In some embodiments of the second apparatus, the generation of the draw control signal, the eject control signal, the first valve control signal, the second valve control signal, and the third valve control signal in the controlled sequence controls the pump and the at least one valve to implement the steps of: (a) drawing a first volume of saline into the chamber via the second inlet port and via the third port of the at least one valve; (b) subsequent to step (a), ejecting at least a portion of the first volume of saline out of the chamber to de-air the chamber; (c) subsequent to step (b), drawing a second volume of saline into the chamber via the second inlet port and via the third port of the at least one valve; (d) subsequent to step (c), ejecting a first portion of the second volume of saline out of the chamber and out of the first inlet port via the first port of the at least one valve to de-air the first inlet port; (e) subsequent to step (c), ejecting a second portion of the second volume of saline out of the chamber and out of the first outlet port via the second port of the at least one valve to de-air the first outlet port; (f) subsequent to steps (d) and (e), and subsequent to a connection of an external syringe filled with a fluid containing embolic beads to the first inlet port, drawing a fluid containing embolic beads into the chamber via the first inlet port and the first port of the at least one valve; and (g) subsequent to step (f), ejecting the fluid containing the embolic beads out of the chamber and out of the first outlet port via the second port of the at least one valve. In some of these embodiments, the generation of the draw control signal, the eject control signal, the first valve control signal, the second valve control signal, and the third valve control signal in the controlled sequence also controls the pump and the at least one valve to implement the steps of: (h) subsequent to step (g), drawing a third volume of saline into the chamber via the second inlet port and via the third port of the at least one valve; and (i) subsequent to step (h), ejecting at least a portion of the third volume of saline out of the chamber and out of the first outlet port via the second port of the at least one valve.

Some embodiments of the second apparatus further comprise a sensor arranged to detect when the external syringe is connected to the first inlet port and report a connection status of the external syringe to the controller.

Some embodiments of the second apparatus further comprise a pressure gauge arranged to measure a fluid pressure of fluid exiting the first outlet port and report a fluid pressure measurement to the controller.

Some embodiments of the second apparatus further comprise a drain port and a second fluid flow path arranged to route fluid from the third port of the at least one valve to the drain port, wherein the first fluid flow path includes a first check valve, and the second fluid flow path includes a second check valve.

In some embodiments of the second apparatus, the at least one valve comprises a rotary valve having at least three positions, and the valve actuator comprises a motor configured to move the rotary valve between the at least three positions.

Some embodiments of the second apparatus further comprise a sensor arranged to detect when the external syringe is connected to the first inlet port and report a connection status of the external syringe to the controller, a pressure gauge arranged to measure a fluid pressure of fluid exiting the first outlet port and report a fluid pressure measurement to the controller, a drain port, and a second fluid flow path arranged to route fluid from the third port of the at least one valve to the drain port. In these embodiments, the first fluid flow path includes a first check valve, and the second fluid flow path includes a second check valve. In some of these embodiments, the generation of the draw control signal, the eject control signal, the first valve control signal, the second valve control signal, and the third valve control signal in the controlled sequence controls the pump and the at least one valve to implement the steps of: (a) drawing a first volume of saline into the chamber via the second inlet port and via the third port of the at least one valve; (b) subsequent to step (a), ejecting at least a portion of the first volume of saline out of the chamber via the drain port to de-air the chamber; (c) subsequent to step (b), drawing a second volume of saline into the chamber via the second inlet port and via the third port of the at least one valve; (d) subsequent to step (c), ejecting a first portion of the second volume of saline out of the chamber and out of the first inlet port via the first port of the at least one valve to de-air the first inlet port; (e) subsequent to step (c), ejecting a second portion of the second volume of saline out of the chamber and out of the first outlet port via the second port of the at least one valve to de-air the first outlet port; (f) subsequent to steps (d) and (e), and subsequent to a connection of an external syringe filled with a fluid containing embolic beads to the first inlet port, drawing a fluid containing embolic beads into the chamber via the first inlet port and the first port of the at least one valve; and (g) subsequent to step (f), ejecting the fluid containing the embolic beads out of the chamber and out of the first outlet port via the second port of the at least one valve, and the controller is configured to abort step (g) if the fluid pressure measurement reported to the controller exceeds a threshold.

In some of these embodiments, the generation of the draw control signal, the eject control signal, the first valve control signal, the second valve control signal, and the third valve control signal in the controlled sequence also controls the pump and the at least one valve to implement the steps of: (h) subsequent to step (g), drawing a third volume of saline into the chamber via the second inlet port and via the third port of the at least one valve; and (i) subsequent to step (h), ejecting at least a portion of the third volume of saline out of the chamber and out of the first outlet port via the second port of the at least one valve.

BRIEF DESCRIPTION OF THE DRAWINGS

Various embodiments are described in detail below with reference to the accompanying drawings, wherein like reference numerals represent like elements.

DESCRIPTION OF THE PREFERRED EMBODIMENTS

Figure 1:
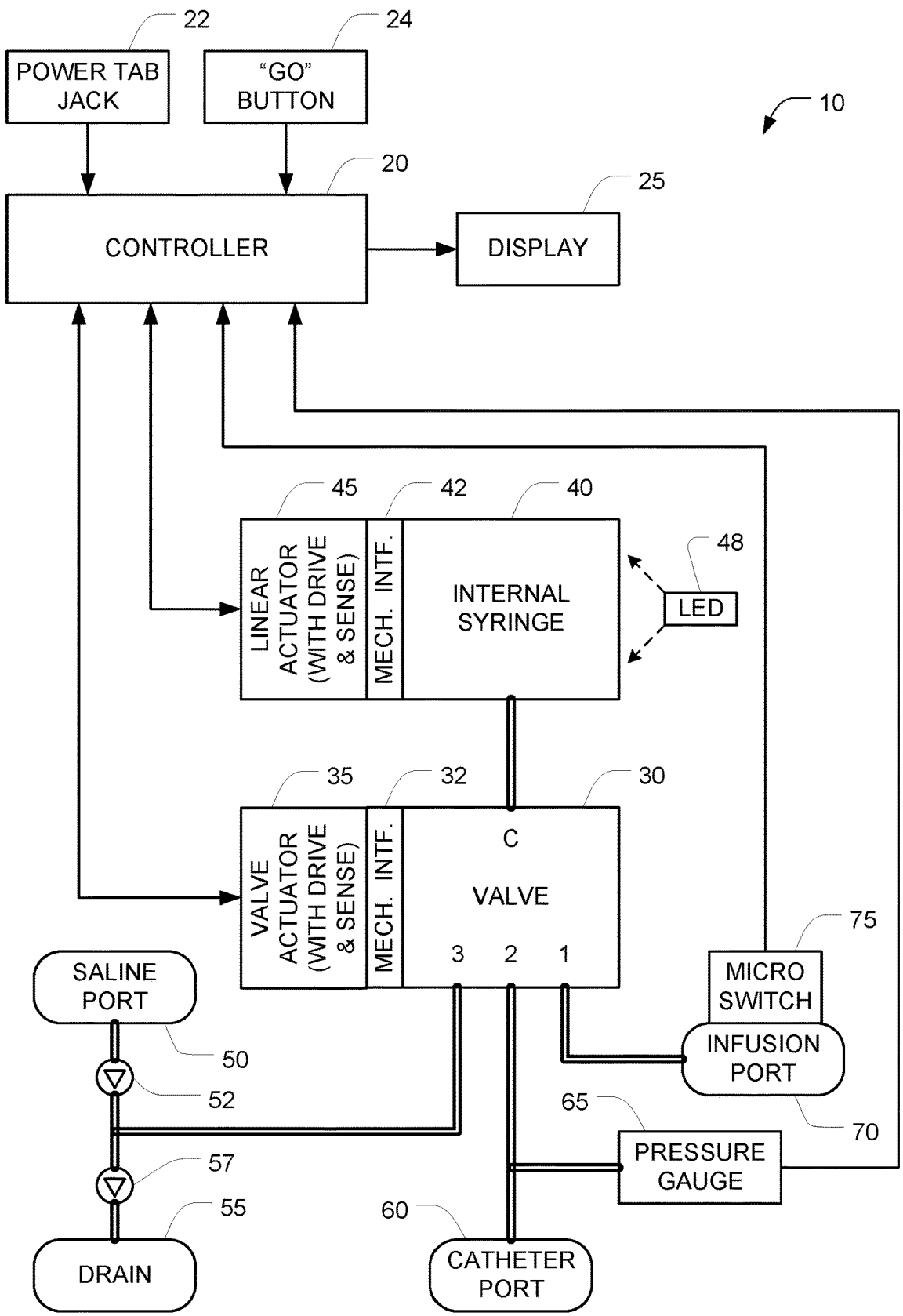
FIG. 1 is a block diagram of an embodiment for controlling the delivery of embolic beads into a subject's artery.

FIG. 1 is a block diagram of an apparatus 10 for controlling the delivery of embolic beads into a subject's artery via a lumen of a catheter. Note that fluid flow paths in FIG. 1 are indicated using double lines, while electrical signals and data flow paths are indicated using single lines. One possible use for this apparatus 10 is to deliver embolic beads to the distal portion of a subject's left gastric artery in order to achieve a reduction in the production of Ghrelin. A wide variety of alternative uses are also possible in different portions of a subject's vasculature.

In some preferred embodiments, the apparatus 10 is a single-use, disposable device that is powered by internal batteries (not shown). The apparatus 10 automatically executes an injection sequence of embolic particles and fluid through a catheter (e.g., an occlusion balloon catheter).

The apparatus 10 includes an internal syringe 40, and this syringe has a chamber configured to hold fluid. The chamber has an orifice through which fluid enters and exits the chamber of the syringe 40. The internal syringe 40 also has a plunger configured to draw fluid into the chamber via the orifice when the plunger is withdrawn and eject fluid out of the chamber via the orifice when the plunger is advanced. In some embodiments, the body of the internal syringe 40 is made of a translucent or transparent medical grade plastic such as polycarbonate, and the plunger of the internal syringe 40 is dimensioned to fit in the barrel of the internal syringe 40 (as it does in an ordinary syringe). In some embodiments, the chamber of the syringe is sized to accommodate between 5 and 10 cc of fluid when the plunger is fully withdrawn.

A linear actuator 45 is operatively connected to the plunger via a mechanical interface 42 such that the linear actuator can either withdraw the plunger, advance the plunger, or leave the plunger in a stationary position. The withdrawal of the plunger is initiated when the linear actuator 45 receives a draw control signal from the controller 20, and the advancing of the plunger is initiated when the linear actuator 45 receives an eject control signal from the controller 20. (The generation of the draw control signal and the eject control signal is described below in connection with the controller 20.) When the linear actuator 45 withdraws the plunger, fluid will be drawn into the chamber. When the linear actuator 45 advances the plunger, fluid will be ejected from the chamber.

In some embodiments, the linear actuator 45 is implemented using a non-captive linear actuator such as a Haydon Kerk 21F4AB-2.5-A07 actuator. The linear actuator 45 also includes driver electronics configured so that low-level signals can be used to move the linear actuator in either direction so as to advance or withdraw the plunger. A wide variety of formats for these low-level signals can be readily envisioned. In one example, the controller 20 can generate the draw control signal and the eject control signal by writing specific control words to one or more memory mapped control addresses. In another example, the controller has one dedicated output line that, when asserted, causes the linear actuator 45 to advance the plunger and a second dedicated output line that, when asserted, causes the linear actuator 45 to withdraw the plunger. The driver electronics receives the draw control signal and the eject control signal from the controller 20 and generates appropriate electrical signals that cause the actuator to move. Details of the implementation of the linear actuator 45 and the driver electronics for the linear actuator will be apparent to persons skilled in the relevant arts.

The nature of the mechanical interface 42 between the linear actuator 45 and the internal syringe 40 will depend on the type of linear actuator that is used and the mechanical configuration of the internal syringe 40. Similarly, the nature of the driver electronics contained within the linear actuator 45 will depend on the type of linear actuator that is used (e.g., motor, stepper motor, etc.).

Optionally, the linear actuator 45 includes one or more sensing elements that can be used to verify that the internal syringe 40 has been moved to the desired position in response to the draw and eject control signals. Examples of suitable sensing elements for this purpose include optical encoders, magnetic encoders, resolvers, a plate connected to a sliding shaft with slots that either permit light to travel between an emitter and a photodetector block or block that light, etc. If, at any time, feedback from the sensing element indicates that the internal syringe 40 has not moved to a desired position in response to a command, the controller 20 can take appropriate action to try to get the syringe to move to the desired position (e.g., re-issuing an appropriate control signal).

In alternative embodiments, a different type of pump may be used in place of the internal syringe 40 and the linear actuator 45. Examples include but are not limited to rotary pumps, reciprocal pumps, positive displacement pumps, peristaltic pumps, etc. These alternative pumps are configured to draw fluid into a chamber in response to a draw control signal and eject fluid from the chamber in response to an eject control signal. In embodiments that do not use a syringe for the pump, a different type of actuator may be used in place of the linear actuator 45 depicted in FIG. 1. Implementation of the actuator will be apparent to persons skilled in the relevant arts, depending on the type of pump that is used. In these embodiments, appropriate driver electronics for driving those pumps in response to the draw control signal and the eject control signal are included, the nature of which will be apparent to persons skilled in the relevant arts, depending on the type of pump that is used.

As will be appreciated by persons skilled in the relevant arts, the nature of the chamber will vary depending on the type of pump being used. For example, in the case of peristaltic pumps, the chamber may be a section of tubing within the peristaltic pump. In addition, the nature of the draw control signal and the eject control signal may vary depending on the type of pump being used. For example, in the case of peristaltic pumps that draw and eject simultaneously, a single unified control signal may serve as both the draw control signal and the eject control signal.

Optionally, any of these alternative embodiments may include appropriate sensing electronics that permit the controller 20 to determine whether the pump has executed a command that it received from the controller 20.

Returning to the apparatus depicted in FIG. 1, the apparatus 10 also includes a valve 30 configured to selectively route fluid from one of the three ports (i.e. the first port, the second port or the third port) to a common port. The common port C is arranged in fluid communication with the orifice of the syringe 40. The valve 30 has a first operating state in which a fluid-flow path is provided between the first port and the common port, a second operating state in which a fluid-flow path is provided between the second port and the common port, and a third operating state in which a fluid-flow path is provided between the third port and the common port. In some embodiments, the valve 30 has additional states in which a fluid path is provided between additional ports (not shown) and the common port. In some preferred embodiments, the valve 30 is a three position rotary valve. In other embodiments, the valve 30 is a four position rotary valve, and one of the positions is not used. In alternative embodiments, non-rotary valves (e.g., a three position valve that operates by sliding a slider) may be used.

In other alternative embodiments (not shown), instead of using a single valve that has multiple positions (e.g., three positions), a plurality of valves may be arranged to achieve a similar end result. More specifically, the plurality of valves are interconnected to provide a common port arranged in fluid communication with the orifice of the internal syringe 40 (or an alternative pump), as well as a first port, a second port, and a third port. The plurality of valves, taken together, has a first operating state in which a fluid-flow path is provided between the first port and the common port, a second operating state in which a fluid-flow path is provided between the second port and the common port, and a third operating state in which a fluid-flow path is provided between the third port and the common port.

A valve actuator 35 is operatively connected to the valve 30 via a mechanical interface 32. The valve actuator is designed to place the valve in the first operating state (which connects the first port to the common port) in response to a first valve control signal, place the valve in the second operating state (which connects the second port to the common port) in response to a second valve control signal, and place the valve in the third operating state (which connects the third port to the common port) in response to a third valve control signal. The first, second, and third valve control signals are generated by the controller 20 as described below.

In those embodiments where a rotary valve is used as the valve 30, the valve actuator 35 is designed to rotate the valve 30 to the appropriate angular position to connect either the first port, the second port, or the third port to the common port. Examples of suitable components for implementing this rotation include stepper motors and DC motors. Details of the design of the valve actuator 35 and the mechanical interface 32 will be apparent to persons skilled in the relevant art, and will depend on the nature of the design of the valve 30.

In alternative embodiments (not shown) in which a plurality of valves (e.g., 3 individual valves) are used to selectively connect a common port to either a first port, a second port, or a third port, the valve actuator will selectively open and close each of the plurality of valves to set up the desired fluid flow path.

The valve actuator 35 also includes a driver circuit configured so that low-level signals from the controller 20 can be used to move the valve 30 to select the desired port of the valve. A wide variety of formats for these low-level signals can be readily envisioned. In one example, the controller 20 can generate the first, second, and third valve control signals by writing specific control words to one or more memory mapped control addresses. In another example, the controller has three dedicated output lines that, when asserted, respectively cause the valve actuator 35 to move the valve 32 to select either the first port, the second port, or the third port.

The valve actuator 35 will include a component that converts electromagnetic energy into motion (e.g., a DC motor, a stepper motor, a linear actuator, etc.). And the driver circuit in the valve actuator 35 is configured to generate whatever signals are needed to drive that component and make it respond to the low-level signals that arrive from the controller 20. Details of the implementation of the driver circuit for the valve actuator 35 will depend on the nature of the moving component, and will be apparent to persons skilled in the relevant arts.

In some embodiments, the valve actuator 35 also includes one or more sensing elements that can be used to verify that the valve 30 has been moved to the desired position in response to the first, second, and third valve control signals. Examples of suitable sensing elements for this purpose include optical encoders, magnetic encoders, resolvers, a disc connected to a rotating shaft with slots that either permit light to travel between an emitter and a photodetector or block that light, etc. If, at any time, feedback from the sensing element indicates that the valve 30 has not moved to a desired position in response to a command, the controller 20 can take appropriate action to try to get the valve 30 to move to the desired position (e.g., re-issuing an appropriate control signal).

A first inlet port 70 (also referred to herein as an infusion port) is arranged in fluid communication with the first port of the valve. The first inlet port 70 is configured to provide a fluid-tight coupling with an orifice of an external syringe when an external syringe is connected to the first inlet port. The connection between the first inlet port 70 and the first port of the valve 30 may be made, for example, using appropriate medical-grade tubing. In some embodiments, the first inlet port 70 interfaces with the external syringe using a Luer lock coupling. Optionally, the Luer lock coupling may be disposed at the bottom of a well-shaped cavity that is shaped to accept the external syringe (e.g. a 6 cc syringe).

A first outlet port 60 (also referred to herein as a catheter port) is arranged in fluid communication with the second port of the valve, and the first outlet port i 60 s configured to provide a fluid-tight connection with the lumen of the catheter when the catheter is connected to the first outlet port. The connection between the first outlet port 60 and the second port of the valve 30 may be made, for example, using appropriate medical-grade tubing.

A second inlet port 50 (also referred to herein as a saline input port) is arranged to provide a fluid-tight coupling with a source of saline solution. A first fluid flow path is provided to route saline solution arriving via the second inlet port 50 into the third port of the valve 30. The connection between the second inlet port 50 and the third port of the valve 30 may be made, for example, using appropriate medical-grade tubing. In the illustrated embodiment, a check valve 52 (e.g., a spring and plunger check valve) is provided in this path, oriented to prevent saline from exiting via this second inlet port 50.

The illustrated embodiment also includes a drain port 55. A second fluid flow path is provided to route fluid from the third port of the valve 30 to the drain port 55. The connection between the drain port 55 and the third port of the valve 30 may be made, for example, using appropriate medical-grade tubing. In the illustrated embodiment, a check valve 57 (e.g., a spring and plunger check valve) is provided in this path, oriented to prevent saline from entering via the drain port 55. In alternative embodiments, the drain port 55 and the second check valve 57 can be omitted, in which case one of the other ports (e.g., the first inlet port 70 or the first outlet port 60) may be used to implement the drain functions described herein.

A controller 20 is configured to generate the draw control signal, the eject control signal, the first valve control signal, the second valve control signal, and the third valve control signal in a controlled sequence. The controller 20 may be implemented using a microprocessor or a microcontroller that is programmed to implement the sequences of steps described below. The controller 20 has access to sufficient RAM and nonvolatile memory such as ROM, SSD, etc. (not shown). In alternative embodiments (not shown) the controller 20 may be implemented using microprogrammed or hardwired logic.

The controller's 20 generation of the draw control signal, the eject control signal, the first valve control signal, the second valve control signal, and the third valve control signal in the controlled sequence causes the linear actuator 45 and the valve actuator 35 to control the internal syringe 40 and the valve 30, respectively, to implement steps (a) through (g) described below in connection with FIG. 2. In the illustrated embodiment, the controller 20 begins the sequence of steps depicted in FIG. 2 in response to a momentary depression of the GO button 24. Optionally, prior to the depression of the go button 24, the controller 20 may command the display 25 to display an appropriate message (e.g., "connect saline and press go button"). The display 25 may be implemented using any of a wide variety of display technologies including but not limited to LED and LCD displays.

Figure 2:
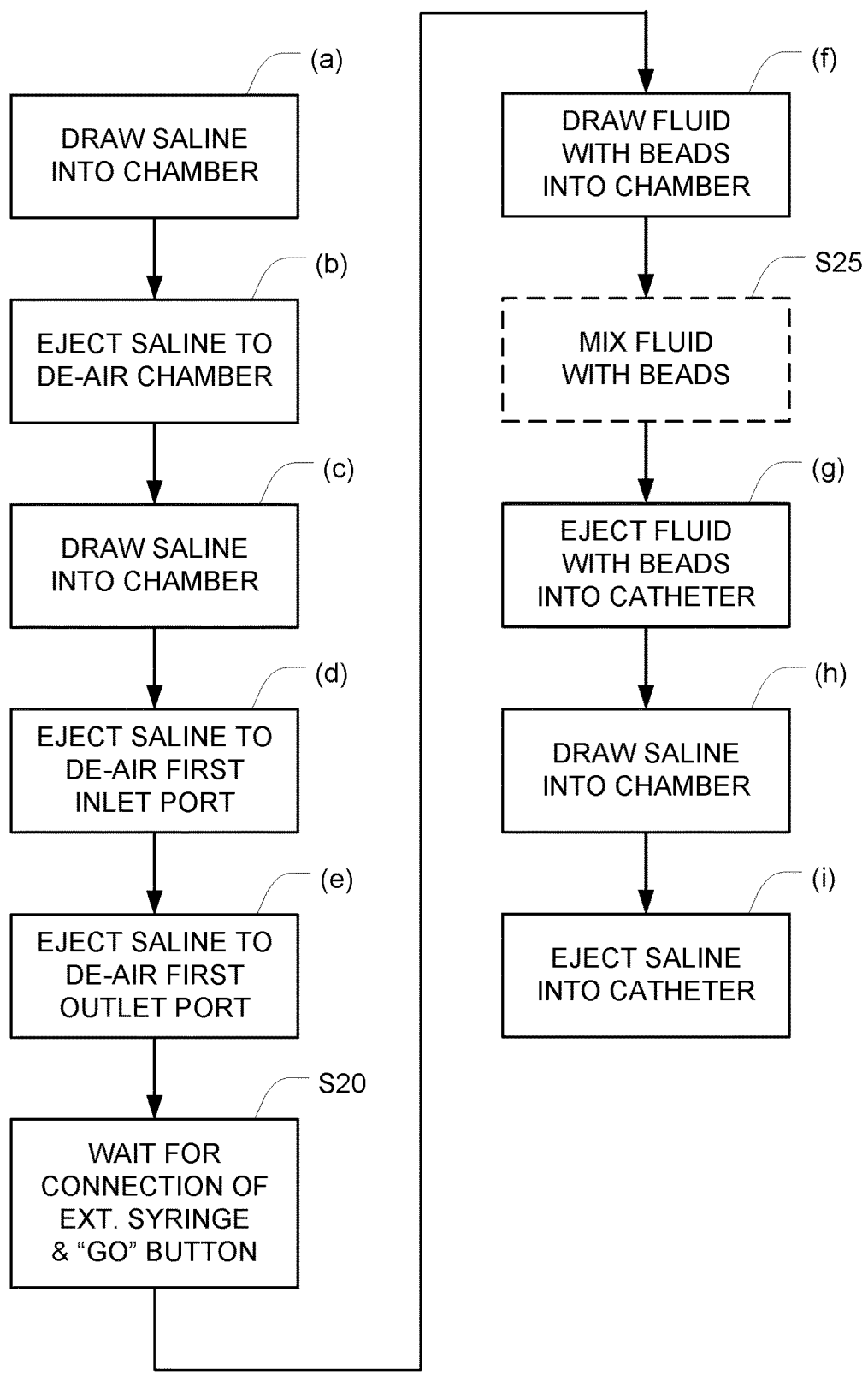
FIG. 2 depicts a sequence of steps that are orchestrated by the controller of the FIG. 1 embodiment.

FIG. 2 depicts a sequence of steps that are orchestrated by the controller 20 of the FIG. 1 embodiment. In the discussion that follows, the numeric reference numbers appear in FIG. 1 and the alphanumeric reference numbers appear in FIG. 2.

FIG. 2 begins with the assumption that a source of saline solution has already been connected to the second inlet port 50 (i.e., the saline port) and the go button 24 has been pressed. Step (a) is drawing a first volume of saline into the chamber via the second inlet port 50 and via the third port of the valve 30. In some embodiments, the controller 20 implements this step by issuing the third valve control signal to the valve actuator 35. The valve actuator 35 will respond by moving the valve 30 to a position at which the third port of the valve 30 is connected to the common port. Subsequently, the controller 20 issues the draw control signal to the linear actuator 45. The linear actuator 45 will respond by withdrawing the plunger of the syringe 40, which will draw a first volume of saline (e.g., 6 cc) into the chamber of the syringe 40.

Step (b) is implemented subsequent to step (a). This step (b) involves ejecting at least a portion of the first volume of saline out of the chamber of the internal syringe 40 to de-air that syringe. In some embodiments, the controller 20 implements this step by issuing the third valve control signal to the valve actuator 35. The valve actuator 35 will respond by moving the valve 30 to a position at which the third port of the valve 30 is connected to the common port. Note that if the valve 30 is already set to that position, this portion of the control sequence can be skipped. Subsequently, the controller issues the eject control signal to the linear actuator 45.

The linear actuator 45 will respond by advancing the plunger of the syringe 40, which will eject at least a portion of the first volume of saline out of the chamber of the internal syringe 40 via the drain port 55. In alternative embodiments, the saline may be ejected out of a different port (e.g., the first outlet port 60 or the first inlet port 70), assuming that appropriate changes to the command sequence are made to select those ports. In some embodiments, the linear actuator 45 advances the plunger to the farthest extent possible to eject as much saline as possible.

Optionally, the controller 20 may command the display 25 to display an appropriate message (e.g., "purging air") during steps (a) and (b). In the illustrated embodiment, the controller 20 repeats steps (a) and (b) one or more times to ensure that the internal syringe 40 has been completely de-aired.

Step (c) is implemented subsequent to step (b). This step (c) involves drawing a second volume of saline (e.g., 6 cc) into the chamber of the internal syringe 40 via the second inlet port 50 and via the third port of the valve 30. In some embodiments, the controller 20 implements this step by issuing the third valve control signal to the valve actuator 35. The valve actuator 35 will respond by moving the valve 30 to a position at which the third port of the valve 30 is connected to the common port. (Note that if the valve 30 is already set to that position, this portion of the control sequence can be skipped.) Subsequently, the controller 20 issues the draw control signal to the linear actuator 45. The linear actuator 45 will respond by withdrawing the plunger of the syringe 40, which will draw a second volume of saline into the chamber of the syringe 40.

Step (d) is implemented subsequent to step (c). This step (d) involves ejecting a first portion of the second volume of saline out of the chamber of the internal syringe 40 and out of the first inlet port 70 via the first port of the valve 30 to de-air the first inlet port 70. In some embodiments, the controller 20 implements this step by issuing the first valve control signal to the valve actuator 35. The valve actuator 35 will respond by moving the valve 30 to a position at which the first port of the valve 30 is connected to the common port. (Note that if the valve 30 is already set to that position, this portion of the control sequence can be skipped.) Subsequently, the controller issues the eject control signal to the linear actuator 45. The linear actuator 45 will respond by advancing the plunger of the syringe 40, which will eject a first portion (e.g., the first half, or 3 cc) of the second volume of saline out of the chamber of the internal syringe 40 via the first inlet port 70.

Step (e) is also implemented subsequent to step (c). This step (e) involves ejecting a second portion of the second volume of saline out of the chamber of the internal syringe 40 and out of the first outlet port 60 via the second port of the valve 30 to de-air the first outlet port 60. In some embodiments, the controller 20 implements this step by issuing the second valve control signal to the valve actuator 35. The valve actuator 35 will respond by moving the valve 30 to a position at which the second port of the valve 30 is connected to the common port. (Note that if the valve 30 is already set to that position, this portion of the control sequence can be skipped.) Subsequently, the controller issues the eject control signal to the linear actuator 45. The linear actuator 45 will respond by advancing the plunger of the syringe 40, which will eject a second portion (e.g., the remaining half, or 3 cc) of the second volume of saline out of the chamber of the internal syringe 40 via the first outlet port 60. Note that step (e) may be performed either before or after step (d). Optionally, the controller 20 may command the display 25 to display an appropriate message (e.g., "purging air") during steps (c), (d), and (e).

Optionally, after steps (d) and (e) are performed, the controller 20 may command the display 25 to display a message instructing the user to connect the external syringe to the first inlet port 70 (i.e., the infusion port).

After steps (d) and (e) are performed, the user connects an external syringe filled with a fluid containing embolic beads to the first inlet port 70. In some embodiments, this event is detected by a sensor arranged to detect when the external syringe is connected to the first inlet port 70 and report a connection status of the external syringe to the controller 20. For example, a microswitch 75 may be mounted in proximity to the first inlet port 70 so that the microswitch 75 will be actuated when the external syringe is connected. The controller 20 receives a signal from the microswitch 75 to determine whether or not the external syringe has been connected to the first inlet port 70. The system waits until the external syringe has been connected to the first inlet port 70.

Step (f) is implemented after steps (d) and (e) are performed and after the external syringe has been connected to the first inlet port 70 and the user has pressed the GO button 24 (step S20). In the illustrated embodiment, the controller 20 is programmed to permit the remaining steps (f) through (i) to occur only if the GO button 24 remains depressed. If the user releases the GO button at any point in time, the controller 20 will pause the sequence of steps. In these embodiments, the controller 20 may be programmed to continue the sequence of steps from the point at which it was interrupted if the user presses and holds the GO button 24 again.

Step (f) involves drawing a fluid containing embolic beads into the chamber of the internal syringe 40 via the first inlet port 70 and the first port of the valve 30. Preferably, the fluid also contains a contrast agent to make the fluid visible under fluoroscopy. In some embodiments, the controller 20 implements this step by issuing the first valve control signal to the valve actuator 35. The valve actuator 35 will respond by moving the valve 30 to a position at which the first port of the valve 30 is connected to the common port. (Note that if the valve 30 is already set to that position, this portion of the control sequence can be skipped.) Subsequently, the controller 20 issues the draw control signal to the linear actuator 45. The linear actuator 45 will respond by withdrawing the plunger of the syringe 40, which will draw the fluid containing embolic beads in from the external syringe that has been connected to the first inlet port 70 and into the chamber of the syringe 40. This step (f) ends with a quantity of fluid (e.g., 1.5 cc or 3 cc) in the chamber of the internal syringe 40.

Optionally, a mixing step S25 may be after step (f) and before step (g). One way to implement this mixing step is to have the controller issue the eject control signal to the linear actuator 45. The linear actuator 45 will respond by advancing the plunger of the syringe 40, which will push the fluid containing embolic beads out of the chamber of the internal syringe 40 and back up into the external syringe that is connected to the first inlet port 70. Subsequently, the controller 20 issues the draw control signal to the linear actuator 45 once again. The linear actuator 45 will respond by withdrawing the plunger of the syringe 40, which will draw the fluid containing embolic beads back into the chamber of the syringe 40. This advance/withdraw sequence may be repeated one or more times to ensure complete mixing. This optional mixing step S25 ends with a quantity of fluid (e.g., 1.5 cc or 3 cc) in the chamber of the internal syringe 40.

Optionally, the controller 20 may command the display 25 to display an appropriate message (e.g., "mixing") during step S25.

Step (g) is implemented subsequent to step (f) and, when the optional mixing step S25 is implemented, also subsequent to the mixing step S25. This step (g) involves ejecting the fluid containing the embolic beads out of the chamber of the internal syringe 40 and out of the first outlet port 60 via the second port of the valve 30. In practice, this step (g) should be implemented after the proximal end of a catheter has been connected to the first outlet port 60, and after the distal end of the catheter has been maneuvered into position in the target artery (i.e. the artery into which the embolic beads will be delivered). This step (g) is preferably implemented at a slow and controlled speed so that the injection of embolic beads can be monitored (e.g., using fluoroscopy).

In some embodiments, the controller 20 implements this step (g) by issuing the second valve control signal to the valve actuator 35. The valve actuator 35 will respond by moving the valve 30 to a position at which the second port of the valve 30 is connected to the common port. (Note that if the valve 30 is already set to that position, this portion of the control sequence can be skipped.) Subsequently, the controller issues the eject control signal to the linear actuator 45. The linear actuator 45 will respond by advancing the plunger of the syringe 40, which will eject fluid containing the embolic beads out of the chamber of the internal syringe 40 via the first outlet port 60. The fluid containing the embolic beads will exit the first outlet port 60 and flow through the lumen of the catheter and into the target artery. Optionally, the controller 20 may command the display 25 to display an appropriate message (e.g., "injecting beads") during step (g).

The embolic beads will interfere with the blood flow through the target artery as described in U.S. Pat. No. 9,572,700. When the target artery is the left gastric artery, the reduction in blood flow will reduce the production of ghrelin, which can be advantageous for promoting weight loss.

In the illustrated embodiments, after the fluid containing the embolic beads has been ejected into the catheter in step (g), a quantity of saline is injected into the catheter. This may be accomplished by implementing steps (h) and (i) described below. The purpose of injecting saline into the catheter is to clear the catheter and manifold from residual beads and to prevent clotting.

Step (h) is implemented subsequent to step (g). This step (h) involves drawing a third volume of saline (e.g., 1.5 or 3 cc) into the chamber of the internal syringe 40 via the second inlet port 50 and via the third port of the valve 30. In some embodiments, the controller 20 implements this step by issuing the third valve control signal to the valve actuator 35. The valve actuator 35 will respond by moving the valve 30 to a position at which the third port of the valve 30 is connected to the common port. Subsequently, the controller 20 issues the draw control signal to the linear actuator 45. The linear actuator 45 will respond by withdrawing the plunger of the syringe 40, which will draw a third volume of saline into the chamber of the syringe 40. Optionally, the controller 20 may command the display 25 to display an appropriate message (e.g., "filling with saline") during step (h).

Step (i) is implement subsequent to step (h). This step (i) involves ejecting at least a portion of the third volume of saline out of the chamber of the internal syringe 40 and out of the first outlet port 60 (via the second port of the valve 30) and into the lumen of the catheter. In some embodiments, the controller 20 implements this step by issuing the second valve control signal to the valve actuator 35. The valve actuator 35 will respond by moving the valve 30 to a position at which the second port of the valve 30 is connected to the common port. Subsequently, the controller issues the eject control signal to the linear actuator 45. The linear actuator 45 will respond by advancing the plunger of the syringe 40, which will eject at least a portion of the third volume of saline (e.g., 1.5 or 3 cc) out of the chamber of the internal syringe 40 via the first outlet port 60 and into the lumen of the catheter. Optionally, the controller 20 may command the display 25 to display an appropriate message (e.g., "injecting saline") during step (i).

The illustrated embodiment includes a pressure gauge 65 arranged to measure the fluid pressure of the fluid exiting the first outlet port 60, and to report that fluid pressure measurement to the controller 20. Optionally, the controller 20 may be programmed to abort step (g) or (i) if the fluid pressure measurement reported to the controller exceeds a threshold (e.g., 1000 mbar). One example of a suitable pressure gauge for this purpose is the UTAH DPT-100.

The illustrated embodiment also includes a power switch such as a power tab jack 22. When a plastic male tab is inserted into the jack 22, power from the batteries (not shown) is disconnected from the entire circuit including the controller 20. When the plastic male tab is removed from the jack 22, power from the batteries is connected to the entire circuit. One example of a suitable power jack for this purpose is the Switchcraft 35PM2A-CONN.

Optionally, the body of the internal syringe 40 is made from a transparent or translucent material, and the syringe is mounted behind a clear window so that the status of the internal syringe 40 can be viewed. In these embodiments, an LED 48 may be provided to illuminate the internal syringe 40 to make it easier for users to view the operation of the internal syringe 40. In some embodiments, this LED 48 can be turned on or off by a signal (not shown) from the controller 20. In alternative embodiments, this LED 48 is illuminated any time that power to the overall circuit is on.

A suitable set of operating instructions for using the apparatus 10 is as follows:

1. Remove the pin from the power tab jack 22 and set the pen aside. Verify that the display 25 powers up and is blinking.
2. Press the GO button 24 to toggle through and select a Pre-Programmed injection setting.

Stop toggling once the desired setting is identified. The display 25 will stop blinking after 10 seconds, at which point the apparatus 10 will be set and ready for use. (Note: to change the selection, re-insert the pin into the power tab jack 22 (which will reset the apparatus 10).

3. Connect a saline line to the second inlet port 50 (i.e., the saline port).
4. Connect an Extension Tube Set (e.g., Endobar PN 4831) to the first outlet port 60 (i.e., the catheter port).
5. Prime the internal syringe 40 and fluid conduits by momentarily pressing the GO button one time. This will activate the sequence described above to de-air the fluid conduits using saline.
6. Upon completion of priming, the display 25 will read "Connect Syringe". At this point, the user loads the external syringe filled with 6 cc of a fluid that contains embolic beads into the proper external cavity on the apparatus 10 and secures the external syringe to the Luer fittings on the first inlet port 70 (i.e. the infusion port).

7. Flush and fill the guidewire/infusion lumen of the occlusion balloon catheter shaft with heparinized normal saline.
8. The occlusion balloon catheter is designed to be used coaxially with a steerable guidewires and/or guiding catheters.
9. Introduce the occlusion balloon catheter and guidewire into the patient through a 5F or larger introducer sheath and/or 5F or larger guiding catheter
10. Advance the guidewire and/or guiding catheter and occlusion balloon catheter to a selected vascular site by alternately advancing the guidewire and/or guiding catheter and then tracking the occlusion balloon catheter over the guidewire and/or inside the guiding catheter.
11. Once in position, remove the guidewire and connect the extension line to the infusion Luer of the occlusion balloon catheter.
12. Connect an inflation device containing a 1:1 solution of saline/contrast media to the balloon pressure relief valve female luer and inflate the occlusion balloon to seal against the vessel wall.
13. After placing occlusion balloon catheter into mid portion after origin of esophageal branch left gastric artery angiography will be repeated from guiding catheter and/or occlusion balloon catheter.
14. Activate the apparatus 10 to perform the injection sequence by pressing and holding the GO button 24. (Note: release of the GO button 24 will stop the injection. Re-Pressing the GO button 24 will continue the injection from the same point within the programmed cycle). Mixture of beads and contrast will be injected via the apparatus 10 automatically.
15. If beads and contrast mixture oversaturate vessel, the pressure will increase inside the vessel. The pressure gauge detects this event and reports this condition to the controller. The controller automatically stop the injection.
16. Repeat injections will be performed until stasis of anterograde arterial flow is achieved. The stasis will be evaluated with the balloon deflated.
17. After first injection is completed balloon of the catheter is deflated to allow blood to flow into the artery and to evaluate procedural results.
18. Stasis will be defined as visualization of contrast within the target artery for at least 5 cardiac cycles
19. When sufficient fluid containing embolic particles has been injected, disconnect the line extension from the occlusion balloon catheter.
20. Deflate the occlusion balloon. Confirm fluoroscopically that balloon has completely deflated.
21. Retrieve the occlusion balloon catheter.

Figure 3:
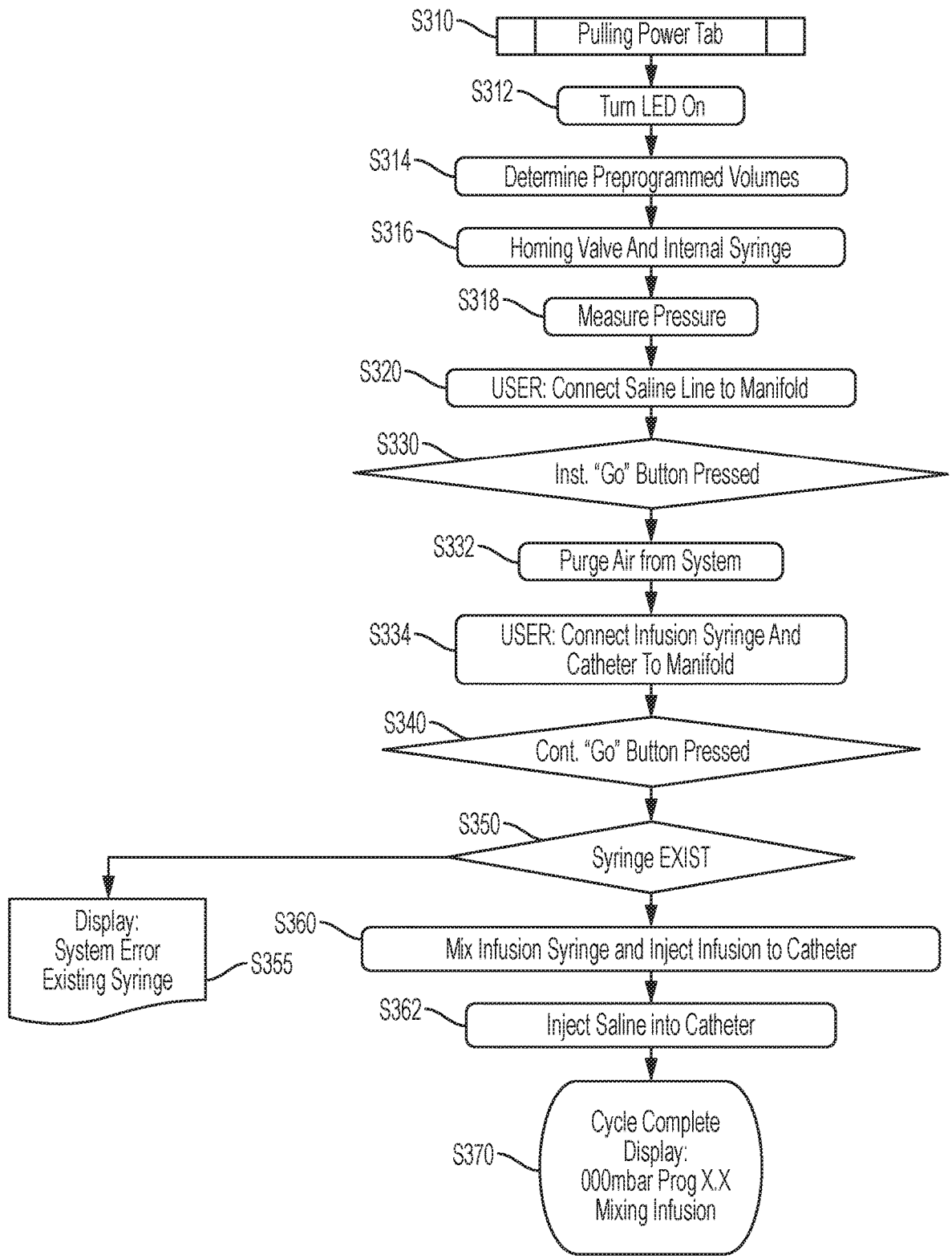
FIG. 3 depicts a flowchart for the delivery of embolic particles using the FIG. 1 embodiment.
Figure 4:
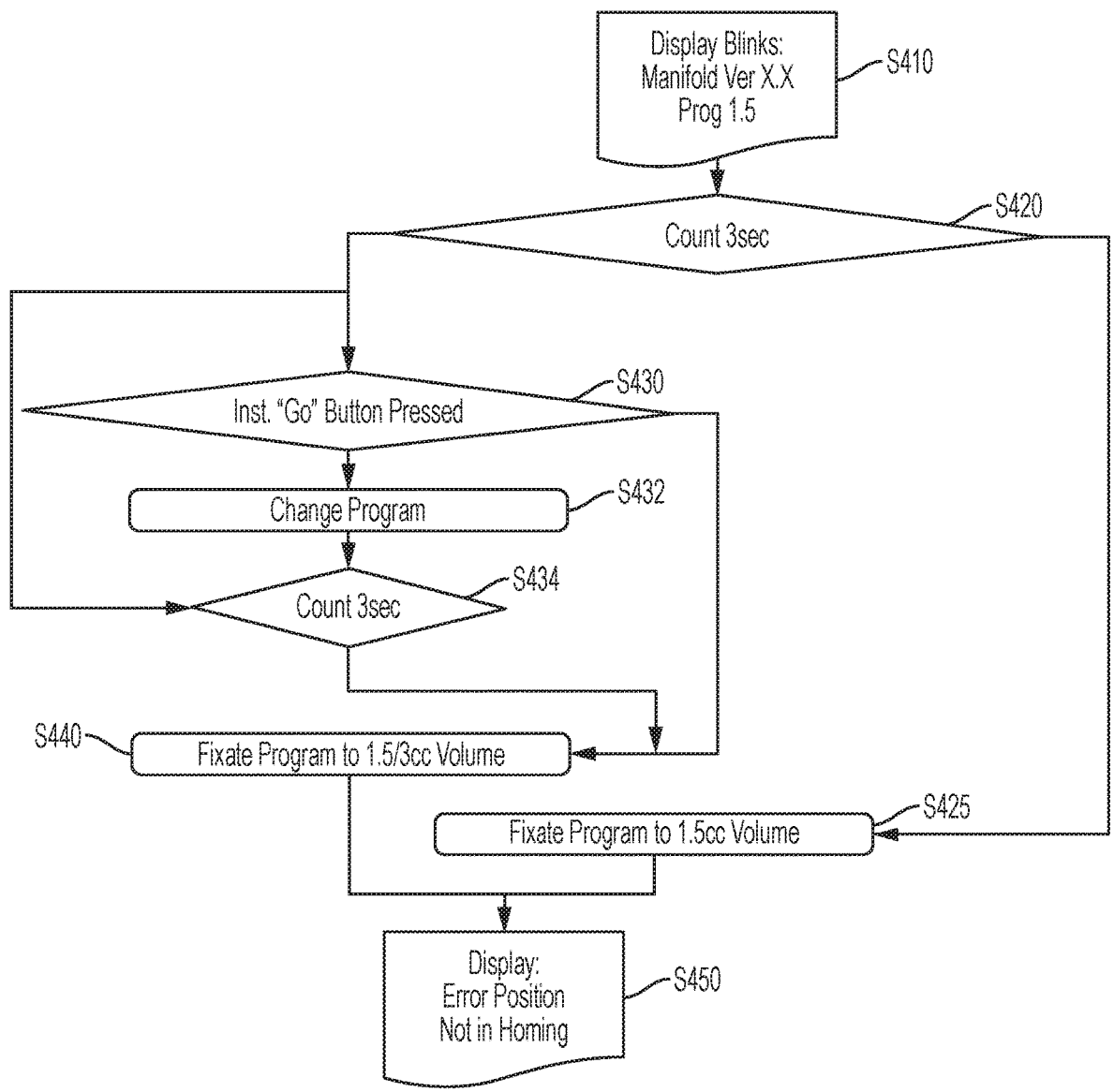
FIG. 4 depicts a flowchart for selecting a volume of fluid that will be delivered using the FIG. 1 embodiment.
Figure 5:
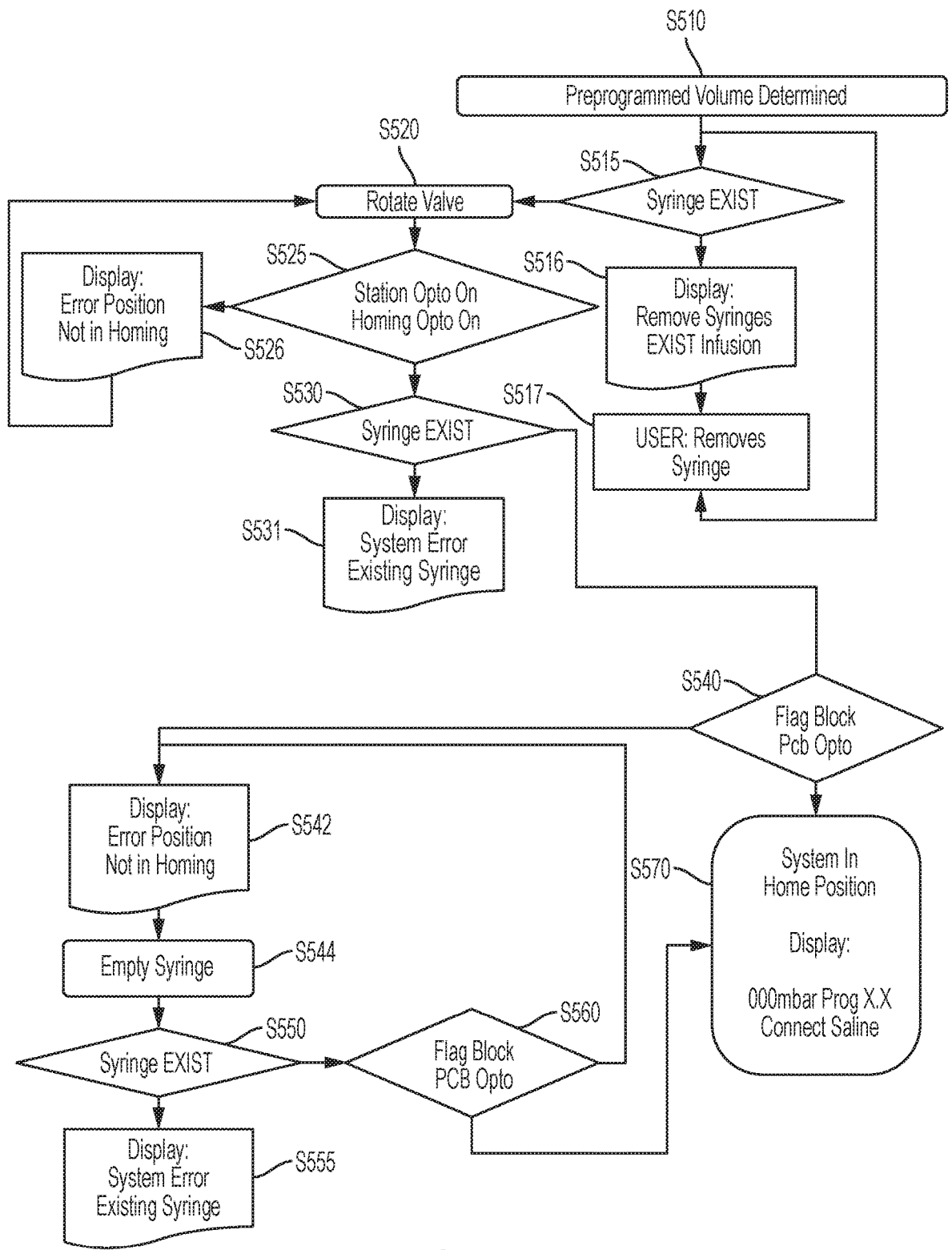
FIG. 5 depicts a flowchart for resetting the components of the FIG. 1 embodiment to a known state prior to use.
Figure 6:
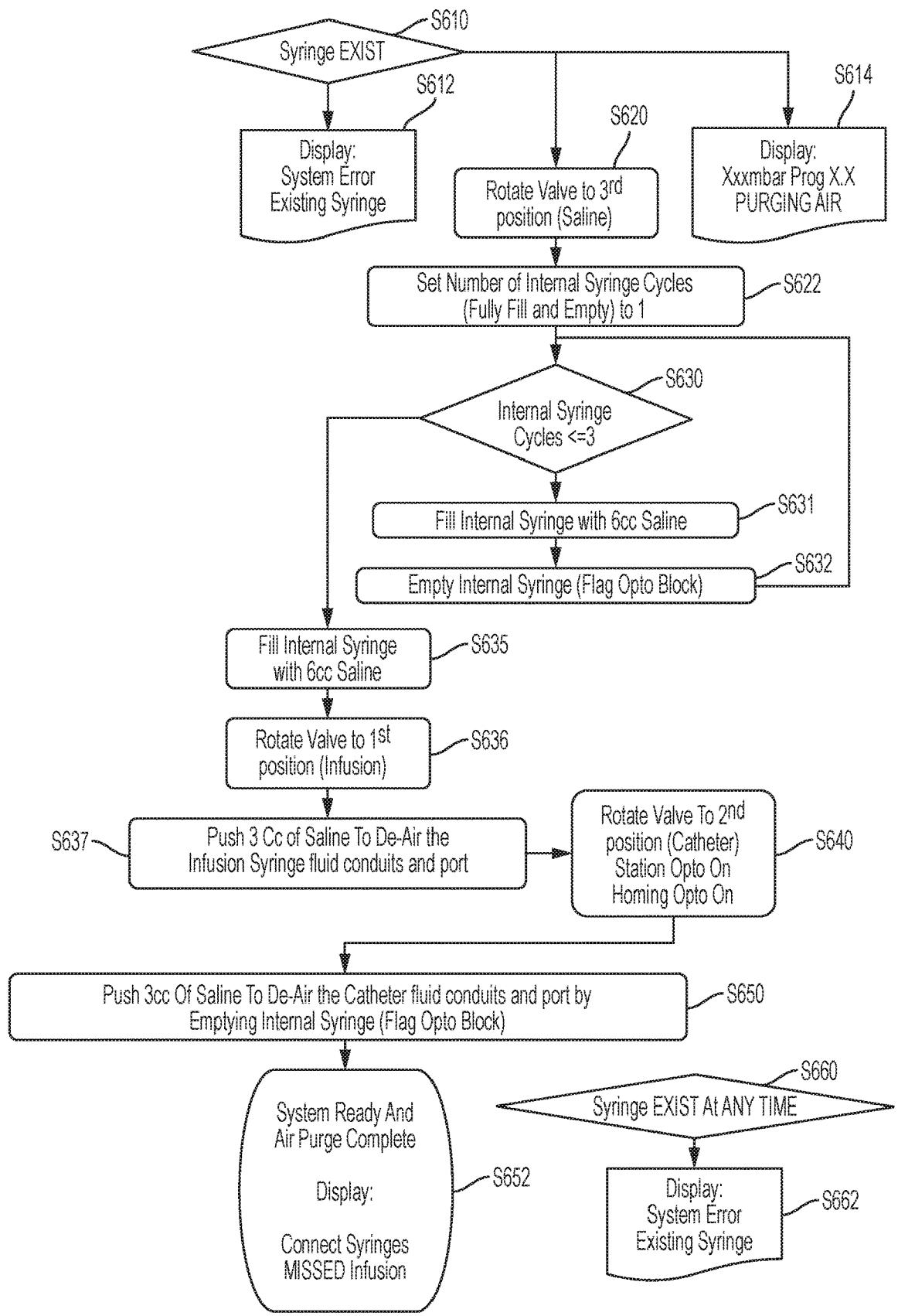
FIG. 6 depicts a flowchart for purging air from the FIG. 1 embodiment.

FIG. 3 depicts a flowchart for the delivery of embolic particles using the FIG. 1 embodiment. Note that in FIGS. 3-8, steps that begin with the word "USER" denote actions that are taken by the user; "Inst." denotes instantaneous; and "Cont." denotes continuous. FIG. 4 depicts a flowchart for selecting a volume of fluid that will be delivered using the FIG. 1 embodiment (e.g., either 1.5 or 3.0 cc). FIG. 5 depicts a flowchart for resetting the valve 30 and internal syringe 40 of the apparatus 10 (all shown in FIG. 1) to a known state prior to use. FIG. 6 depicts a flowchart for purging air from the various paths within the apparatus 10 in the FIG. 1 embodiment.

Figure 7:
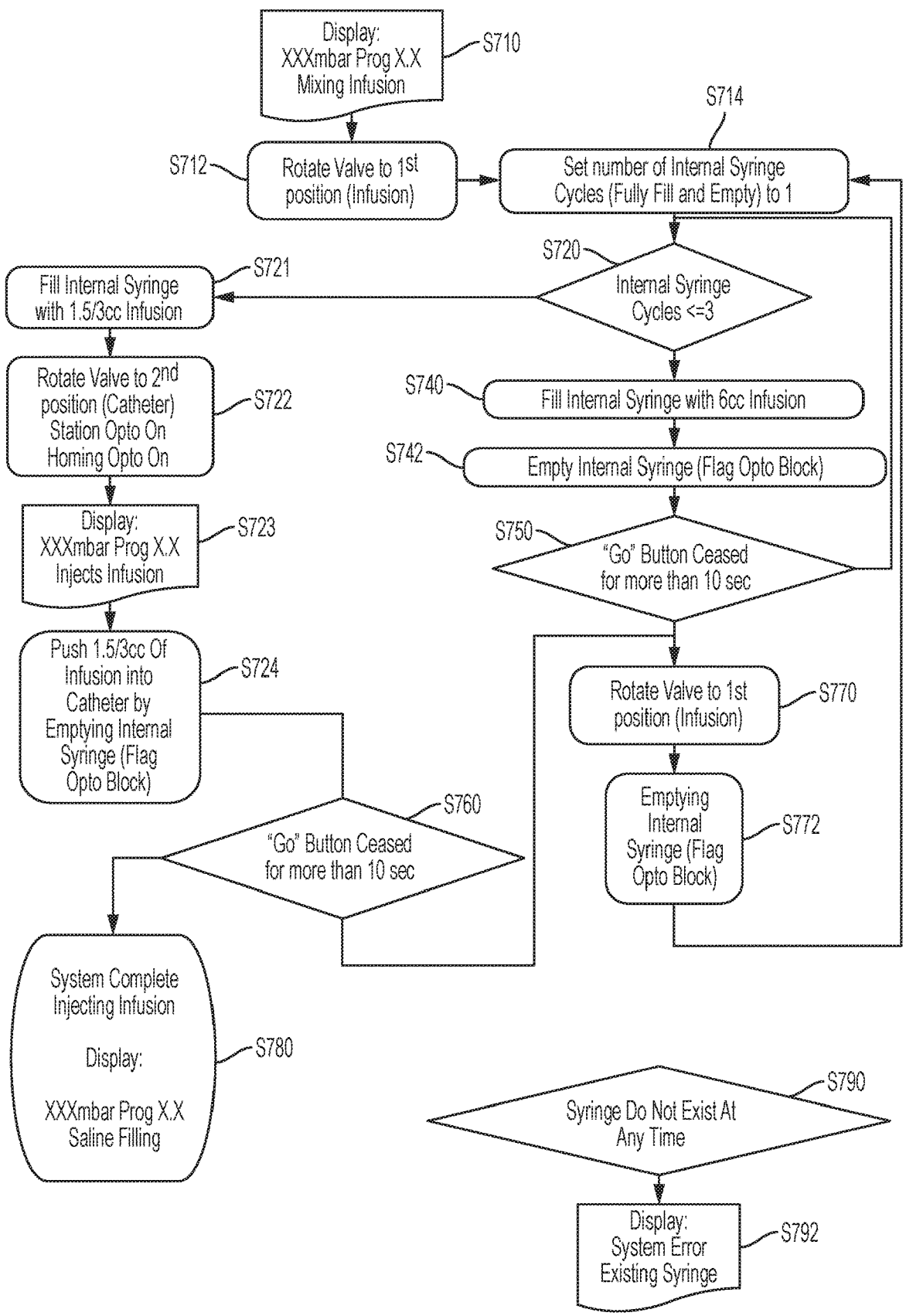
FIG. 7 depicts a flowchart for mixing a fluid containing embolic particles using the FIG. 1 embodiment.
Figure 8:
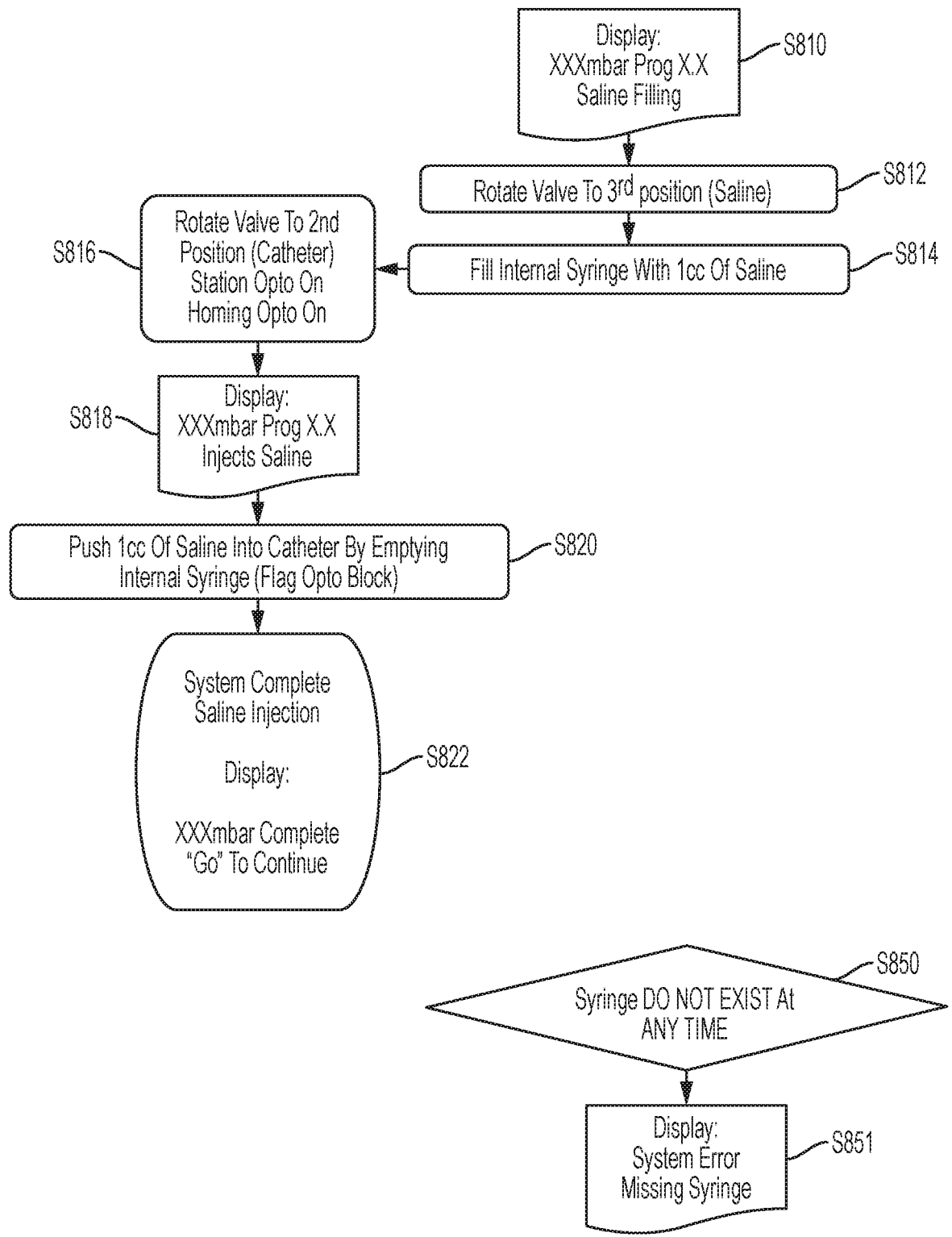
FIG. 8 depicts a flowchart for injecting saline into a catheter using the FIG. 1 embodiment.

FIG. 7 depicts a flowchart for mixing a fluid containing embolic particles in the internal syringe 40 and injecting the infusion out through a catheter that has been connected to the catheter port 60. This flowchart assumes that, prior to step S710, the system is ready for use; purging of air has already been performed; the user has connected and infusion syringe with embolic beads to the infusion port 70; and the user has connected a catheter to the catheter port 60. FIG. 8 depicts a flowchart for filling the internal syringe 40 with saline and injecting saline out through the catheter via the catheter port 60. This flowchart assumes that, prior to step 810, the infusion has already been injected out through the catheter port 60 (e.g., using the process depicted in FIG. 7).

Note that the steps discussed above in connection with FIGS. 2-8 are described in the context of the FIG. 1 embodiment, which uses an internal syringe 40 coupled to a linear actuator 45, and a 3-position valve 30. But in alternative embodiments that replace one or more of those components with an appropriate substance to (e.g., as described above in connection with FIG. 1), appropriate modifications should be made to the sequences of steps, the nature of which will be apparent to persons skilled in the relevant arts.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:
1. An apparatus for controlling delivery of embolic beads into a subject's artery via a lumen of a catheter, the apparatus comprising:
   a pump configured to draw fluid into a chamber in response to a draw control signal and eject the fluid from the chamber in response to an eject control signal;
   at least one valve having a common port arranged in fluid communication with the pump, a first port, a second port, and a third port, wherein the at least one valve has a first operating state in which a fluid-flow path is provided between the first port and the common port, a second operating state in which a fluid-flow path is provided between the second port and the common port, and a third operating state in which a fluid-flow path is provided between the third port and the common port;
   a valve actuator operatively connected to the at least one valve such that the valve actuator (i) places the at least one valve in the first operating state in response to a first valve control signal, (ii) places the at least one valve in the second operating state in response to a second valve control signal, and (iii) places the at least one valve in the third operating state in response to a third valve control signal;
   a first inlet port arranged in fluid communication with the first port of the at least one valve, wherein the first inlet port is configured to provide a fluid-tight coupling with an orifice of an external syringe when the external syringe is connected to the first inlet port;
   a first outlet port arranged in fluid communication with the second port of the at least one valve, wherein the first outlet port is configured to provide a fluid-tight connection with the lumen of the catheter when the catheter is connected to the first outlet port;
   a second inlet port arranged to provide a fluid-tight coupling with a source of saline solution;

a first fluid flow path arranged to route the saline solution arriving via the second inlet port into the third port of the at least one valve; and a controller configured to generate the draw control signal, the eject control signal, the first valve control signal, the second valve control signal, and the third valve control signal in a controlled sequence to control the pump and the at least one valve to implement the steps of (f) subsequent to a connection of an external syringe filled with a fluid containing embolic beads to the first inlet port, drawing the fluid containing embolic beads into the chamber via the first inlet port and the first port of the at least one valve, and (g) ejecting the fluid containing the embolic beads out of the chamber and out of the first outlet port via the second port of the at least one valve.

2. The apparatus of claim 1, wherein generation of the draw control signal, the eject control signal, the first valve control signal, the second valve control signal, and the third valve control signal in the controlled sequence controls the pump and the at least one valve to implement, prior to step (f), the steps of:
(a) drawing a first volume of saline into the chamber via the second inlet port and via the third port of the at least one valve,
(b) subsequent to step (a), ejecting at least a portion of the first volume of saline out of the chamber to de-air the chamber,
(c) subsequent to step (b), drawing a second volume of saline into the chamber via the second inlet port and via the third port of the at least one valve,
(d) subsequent to step (c), ejecting a first portion of the second volume of saline out of the chamber and out of the first inlet port via the first port of the at least one valve to de-air the first inlet port,
(e) subsequent to step (c), ejecting a second portion of the second volume of saline out of the chamber and out of the first outlet port via the second port of the at least one valve to de-air the first outlet port.

3. The apparatus of claim 2, wherein the generation of the draw control signal, the eject control signal, the first valve control signal, the second valve control signal, and the third valve control signal in the controlled sequence also controls the pump and the at least one valve to implement the steps of:
(h) subsequent to step (g), drawing a third volume of saline into the chamber via the second inlet port and via the third port of the at least one valve, and
(i) subsequent to step (h), ejecting at least a portion of the third volume of saline out of the chamber and out of the first outlet port via the second port of the at least one valve.

4. The apparatus of claim 1, further comprising a sensor arranged to detect when the external syringe is connected to the first inlet port and report a connection status of the external syringe to the controller.

5. The apparatus of claim 1, further comprising a pressure gauge arranged to measure a pressure of fluid exiting the first outlet port and report the measured pressure to the controller.

6. The apparatus of claim 1, further comprising:
a drain port; and
a second fluid flow path arranged to route the fluid from the third port of the at least one valve to the drain port,
wherein the first fluid flow path includes a first check valve, and wherein the second fluid flow path includes a second check valve.

7. The apparatus of claim 1, wherein the at least one valve comprises a rotary valve having at least three positions, and wherein the valve actuator comprises a motor configured to move the rotary valve between the at least three positions.

8. The apparatus of claim 1, further comprising:
a sensor arranged to detect when the external syringe is connected to the first inlet port and report a connection status of the external syringe to the controller;
a pressure gauge arranged to measure a fluid pressure of fluid exiting the first outlet port and report a fluid pressure measurement to the controller;
a drain port; and
a second fluid flow path arranged to route fluid from the third port of the at least one valve to the drain port,
wherein the first fluid flow path includes a first check valve, and wherein the second fluid flow path includes a second check valve.

9. The apparatus of claim 8, wherein generation of the draw control signal, the eject control signal, the first valve control signal, the second valve control signal, and the third valve control signal in the controlled sequence controls the pump and the at least one valve to implement, prior to step (f), the steps of:
(a) drawing a first volume of saline into the chamber via the second inlet port and via the third port of the at least one valve,
(b) subsequent to step (a), ejecting at least a portion of the first volume of saline out of the chamber via the drain port to de-air the chamber,
(c) subsequent to step (b), drawing a second volume of saline into the chamber via the second inlet port and via the third port of the at least one valve,
(d) subsequent to step (c), ejecting a first portion of the second volume of saline out of the chamber and out of the first inlet port via the first port of the at least one valve to de-air the first inlet port,
(e) subsequent to step (c), ejecting a second portion of the second volume of saline out of the chamber and out of the first outlet port via the second port of the at least one valve to de-air the first outlet port,
and wherein the controller is configured to abort step (g) if the fluid pressure measurement reported to the controller exceeds a threshold.

10. The apparatus of claim 9, wherein the generation of the draw control signal, the eject control signal, the first valve control signal, the second valve control signal, and the third valve control signal in the controlled sequence also controls the pump and the at least one valve to implement the steps of:
(h) subsequent to step (g), drawing a third volume of saline into the chamber via the second inlet port and via the third port of the at least one valve, and
(i) subsequent to step (h), ejecting at least a portion of the third volume of saline out of the chamber and out of the first outlet port via the second port of the at least one valve.

* * * * *